United States Patent
Top

(10) Patent No.: US 11,402,444 B2
(45) Date of Patent: Aug. 2, 2022

(54) ARRANGEMENT ALLOWING THE PERFORMANCE OF BOTH MAGNETIC PARTICLE IMAGING AND MAGNETIC RESONANCE IMAGING AND A DEVICE COMPRISING THIS ARRANGEMENT

(71) Applicant: ASELSAN ELEKTRONIK SAN. VE TIC. A. S., Ankara (TR)

(72) Inventor: Can Baris Top, Ankara (TR)

(73) Assignee: ASELSAN ELEKTRONIK SAN. VE TIC. A. S., Ankara (TR)

(*) Notice: Subject to any disclaimer, the term of this patent is extended or adjusted under 35 U.S.C. 154(b) by 0 days.

(21) Appl. No.: 17/244,978

(22) Filed: Apr. 30, 2021

(65) Prior Publication Data
US 2021/0356536 A1 Nov. 18, 2021

(30) Foreign Application Priority Data
May 13, 2020 (TR) .................. 2020/07444

(51) Int. Cl.
*G01R 33/00* (2006.01)
*G01R 33/12* (2006.01)
*G01R 33/389* (2006.01)
*G01R 33/44* (2006.01)

(52) U.S. Cl.
CPC ....... *G01R 33/1276* (2013.01); *G01R 33/389* (2013.01); *G01R 33/445* (2013.01)

(58) Field of Classification Search
CPC .............. G01R 33/543; G01R 33/5608; G01R 33/4828; G01R 33/3415; G01R 33/283; G01R 33/307; G01R 33/60; G01R 33/1276; G01R 33/389; G01R 33/445; G01V 3/32; E21B 49/08; E21B 2049/085; G01N 24/10
See application file for complete search history.

(56) References Cited

U.S. PATENT DOCUMENTS

| | | | |
|---|---|---|---|
| 2015/0276902 A1* | 10/2015 | Weaver | G01R 33/4808 324/309 |
| 2015/0316628 A1* | 11/2015 | Heidenreich | A61B 5/0035 324/318 |
| 2018/0148795 A1* | 5/2018 | Hoffmann | G16B 99/00 |

* cited by examiner

*Primary Examiner* — Jermele M Hollington
*Assistant Examiner* — Taqi R Nasir
(74) *Attorney, Agent, or Firm* — Bayramoglu Law Offices LLC

(57) ABSTRACT

An arrangement that enables performing of both magnetic particle imaging and magnetic resonance imaging and a device including the arrangement are provided. The arrangement that enables performance of both magnetic particle imaging and magnetic resonance imaging includes: at least one primary magnetic element pair configured to generate a selection magnetic field (SMF1/SMF2) for magnetic particle imaging, at least one secondary magnetic element pair configured to generate a driving magnetic field, and at least one tertiary magnetic element pair configured to generate a focus magnetic field (FMF).

20 Claims, 9 Drawing Sheets

ARRANGEMENT ALLOWING THE PERFORMANCE OF BOTH MAGNETIC PARTICLE IMAGING AND MAGNETIC RESONANCE IMAGING AND A DEVICE COMPRISING THIS ARRANGEMENT

CROSS REFERENCE TO THE RELATED APPLICATIONS

This application is based upon and claims priority to Turkish Patent Application No. 2020/07444, filed on May 13, 2020, the entire contents of which are incorporated herein by reference.

TECHNICAL FIELD

The present invention relates to an arrangement that enables performing both magnetic particle imaging and magnetic resonance imaging and a device comprising said arrangement.

BACKGROUND

Magnetic particle imaging (MPI) is a relatively new imaging method that enables imaging of nanoscale magnetic particles injected into the body (Gleich, B. And Weizenecker, J. (2005), "Tomographic imaging using the nonlinear response of magnetic particles" in Nature, vol. 435, pp. 1214-1217). Magnetic particle imaging method provides high space and time resolution, and has various uses such as angiography, interventional radiology, tumor imaging and treatment, and perfusion imaging. On the other hand, magnetic particle imaging method can only image the distribution of magnetic nanoparticles, but it does not provide information about anatomy.

Magnetic particle imaging method is preferably based on the rapid and nonlinear magnetization of superparamagnetic iron oxide particles. In order to visualize the particles, a non-homogeneous magnetic field is first created that comprises a point or a line (field-free point or field-free line) where the magnetic field is zero. The magnetic field-free line (FFL) has two main advantages compared to the magnetic field-free point (FFP): a higher signal-to-noise ratio, and a faster scanning of a large area. The region containing a magnetic field-free point or a magnetic field-free line is also called the magnetic field-free region. The magnetic field distribution, which includes a magnetic field-free region, is called the "Selection Field" because it selects the spatial region to be imaged. The superparamagnetic iron oxide particles in the magnetic field-free region can be magnetized with an external magnetic field, while the superparamagnetic iron oxide particles outside the magnetic field-free region cannot react to an external magnetic field since they are magnetically saturated. In magnetic particle imaging method, in addition to the selection field, another magnetic field that changes over time and called the "Drive Field" is also applied. This time-varying magnetic field allows the magnetization of the superparamagnetic iron oxide particles to change dynamically in the magnetic field-free region by exciting these particles. The time-varying magnetization response of the superparamagnetic iron oxide particles is detected by a magnetic receiver. The detected magnetization signal is mainly generated by the superparamagnetic iron oxide particles in the magnetic field-free region and increases in proportion to the particle density. The magnetic field-free region is scanned inside a tissue and the superparamagnetic iron oxide particle distribution in the tissue is obtained by processing the signal received by the magnetic receiver. Field of view can be enlarged by increasing the amplitude of the drive field. On the other hand, the frequency and amplitude of the drive field are limited for patient safety due to concerns on heating and nerve stimulation. Using a drive field amplitude at the frequency range high enough to induce detectable superparamagnetic iron oxide particle signal within the safety limits, the field of view cannot exceed a few centimeters practically. In order to scan a larger field of view, a third magnetic field, which has a much lower frequency but higher amplitude than the drive field is used. Said third magnetic field is called the "Focus Field" because it changes the center position of the imaged region.

Therefore, in the magnetic particle imaging method, in order to collect data from an imaging field that can be used in the clinic and to perform imaging, it is necessary to generate three different magnetic fields: i) an inhomogeneous selection field, ii) an almost homogeneous drive field, and iii) an almost homogeneous focus field.

Magnetic Resonance Imaging (MRI) is a tissue imaging method that has been used as a standard tool in the clinical field. In the state of the art, a highly homogenous magnetic field, rapidly changing magnetic field gradients in three axes, Radio Frequency (RF) transmitting antenna(s) and RF receiving antenna(s) are used for magnetic resonance imaging.

Combining nanoparticle images obtained by magnetic particle imaging method with an anatomical background would be very useful for determining the anatomical location of magnetic particles in clinical use. However, the equipment needed to perform conventional magnetic particle imaging and magnetic resonance imaging methods is quite different. In magnetic resonance imaging, a static magnetic field with high homogeneity; position and time-varying magnetic field in three separate axes; relatively high frequency (preferably about 42.58 MHz per static magnetic field amplitude in Tesla units) transmitting antenna(s) for the generation of the RF signal; and RF receiving antenna(s) to receive the tissue-derived signal are required. In magnetic particle imaging, an inhomogeneous static magnetic field in which the field is very low (even zeroed) in a certain region but high in the other regions is required. In addition, in magnetic particle imaging, a fast time-varying (for example in the frequency range of 1 kHz-200 kHz) homogeneous magnetic field (so called drive field) in three orthogonal axes; and a slow time-varying (for example in the frequency range of 0 Hz-500 Hz) homogeneous magnetic field (so called focus field) in three orthogonal axes are required for three dimensional imaging. Receiver coils in three axes (preferably up to 10 MHz) are also necessary to receive the magnetic response of the particles.

The difference in the magnetic field types and frequency-amplitude values in magnetic particle imaging and magnetic resonance imaging methods hinders the implementation of the same hardware for both magnetic particle imaging and magnetic resonance imaging.

Various methods and systems are proposed in the state of the art in order to combine magnetic particle imaging and magnetic resonance imaging in a single system.

In the state of the art the United States of America U.S. Pat. No. 9,927,500 discloses a system in which a magnet with reverse polarity is placed next to another magnet that generates a homogeneous magnetic field for magnetic resonance imaging. The low magnetic field region required for magnetic particle imaging is formed between said two magnets. Thus, two spatially distinct imaging regions are created for magnetic particle imaging and magnetic resonance imaging. The magnetic resonance image and the magnetic particle image can be obtained sequentially by shifting the imaged object. The combination of magnetic particle images with anatomical images is provided by the alignment of the fiducial markers placed around the object that can be visualized in both magnetic particle and magnetic resonance images. Since the hardware components used for magnetic particle imaging and magnetic resonance imaging in the system disclosed in the mentioned patent document are independent from each other, the system cost is relatively high. In addition, since the magnetic resonance and magnetic particle imaging field of view centers are separate, the patient being imaged must be moved between the said field of view centers and the obtained images must be superimposed. Furthermore, by means of the system disclosed in said patent document, a field-free point, which is less sensitive than a field-free line, is scanned. As a result of this, for a practical human-sized large area scanning scenario, required imaging time is relatively high. Besides, since the patient need to be placed inside a closed bore, it is not suitable for interventional applications.

In the state of the art the United States of America U.S. Pat. No. 10,191,130 discloses an implementation of a two-part resistive solenoid electromagnet to create a homogeneous magnetic field needed in magnetic resonance imaging and an inhomogeneous magnetic field needed in magnetic particle imaging with a single electromagnet. When both parts of said solenoid type electromagnet are fed with the same current, a homogeneous magnetic field is created, which can be used for magnetic resonance imaging purposes. When two parts of the solenoid type electromagnet are fed with opposite currents, a magnetic field gradient is generated, which is suitable for the magnetic particle imaging process. In the system disclosed in said patent document, equipment used for magnetic resonance imaging and magnetic particle imaging process are different from each other except for the said solenoid electromagnet.

Therefore, this is still not a cost-effective solution. In addition, since the electromagnet must be switched to change the mode in order to provide the transition between magnetic resonance imaging and magnetic particle imaging processes, the mode switching process cannot be performed instantaneously. Moreover, by means of the system disclosed in said patent document, the magnetic field-free point is scanned, which is less sensitive than the field-free line, resulting in a relatively high imaging time for the human-sized scanning process. Furthermore, since the patient need to be placed inside a closed bore, it is not suitable for interventional applications.

In the state of the art the United States of America U.S. Pat. No. 8,666,473 discloses a solution proposal for using the same equipment in magnetic resonance imaging and magnetic particle imaging. In the solution disclosed in said document, protons are pre-polarized with a high-amplitude homogeneous magnetic field for a short time (almost 100 ms) using electromagnets or extra electromagnets used in magnetic particle imaging, then the imaging is performed with a low homogeneous magnetic field. Since the magnetic field amplitude is low, the proton resonance frequency and RF frequency decreases to the range of frequencies that can be used in magnetic particle imaging. Thus, the same equipment can be used for magnetic particle imaging and magnetic resonance imaging. In the solution proposed in the aforementioned patent document, a field-free point scanning system is proposed, and 7 pairs of electromagnets are used for 3-dimensional imaging. For magnetic resonance imaging, the coil that generates an inhomogeneous magnetic gradient field for the magnetic particle imaging must be switched into a coil that generates a homogeneous magnetic field, and the focus coils that create a homogeneous magnetic field for magnetic particle imaging must be made to generate a gradient magnetic field for magnetic resonance imaging. There are limitations in performance in both magnetic particle imaging and magnetic resonance imaging, as different magnetic field requirements are tried to be met with said coils. In addition to all these, by means of the system disclosed in said patent document, the magnetic field-free point, which is less sensitive than the magnetic field-free line scanning, is scanned, and this causes the human-sized wide area scanning process to take a long time.

SUMMARY

The aim of the present invention to realize an arrangement that allows performance of both magnetic particle imaging and magnetic resonance imaging and a medical device comprising said arrangement.

The arrangement that allows performance of both magnetic particle imaging and magnetic resonance imaging in order to attain the aim of the present invention, explicated in the first claim and the respective claims hereof, comprises; at least one pair of primary magnetic elements, preferably electromagnet type, which are configured to generate a magnetic selection field, preferably containing a magnetic field-free line for magnetic particle imaging, and to rotate it to the desired angle; at least one pair of secondary magnetic elements, preferably electromagnet-type, configured to generate a time varying magnetic drive field in order to dynamically change the magnetization of the particles in a first plane on which a first axis and a second axis that is substantially perpendicular to the first axis extend; at least one pair of tertiary magnetic elements, preferably electromagnet type, configured to generate the magnetic focus field allowing displacement of the field free region on the first plane wherein in the said arrangement; the primary magnetic element pair can be configured to form a magnetic field gradient in the first plane for magnetic resonance imaging, the secondary magnetic element pair can be configured to form a magnetic field gradient on a third axis perpendicular to the first plane for magnetic resonance imaging, the tertiary magnetic element pair can be configured to create a homogeneous magnetic field for magnetic resonance imaging and the inventive arrangement further comprises; at least one transmitting magnetic element pair, preferably in the form of a coil, configured to excite the nuclear spins in a high homogeneity magnetic field for magnetic resonance imaging, and at least one first receiving magnetic element pair, preferably in the form of a coil, configured to receive magnetic resonance signals from excited nuclear spins for magnetic resonance imaging. In an embodiment of the invention, the secondary magnetic element pair is configured to detect the magnetization response of the magnetic nanoparticles excited in the magnetic particle imaging. In an another embodiment of the invention, the inventive arrangement further comprises at least one second receiving magnetic element pair, preferably in the form of a coil, configured to receive the excited particle signal for magnetic particle imaging. In the magnetic particle imaging process carried out by the inventive arrangement, the magnetization of the magnetic particles in a magnetic field-free region which is formed by the primary magnetic element pair and is preferably in the form of a magnetic field-free line, is dynamically changed by the secondary magnetic element pair and the tertiary magnetic element pair, and the magnetization response of magnetic particles are detected by the secondary magnetic element pair and/or by the second receiving magnetic element pair in order to perform the magnetic particle imaging process. When magnetic resonance imaging is desired to be performed by means of the inventive arrangement, a magnetic field with high homogeneity is generated by feeding current to the tertiary magnetic element pair; currents are applied to the primary magnetic element pair such that a magnetic field gradient at a certain angle to the first axis and the second axis is generated. An imaging section (slice) selection is made on the third axis with the secondary magnetic element pair. Meanwhile, a pulse is applied to the spins by the transmitting magnetic element pair, and after a while another pulse is applied to the spins by the transmitting magnetic element pair. Then, magnetic resonance signal acquisition is performed by means of the first receiving magnetic element pair. The pulses applied by the transmitting magnetic element pair are periodically repeated, and by this way the same radial line in the k-space is scanned several times. The similar sequence is repeated by generating a gradient at different angles with the primary magnetic element pair. Magnetic resonance image is obtained by processing the obtained data using the methods known in the field. This sequence for the magnetic resonance imaging is given only as an example, and different imaging sequences can be performed by a skilled person in the art.

The tertiary magnetic element pair in the inventive arrangement can generate a relatively high homogeneous magnetic field (0.05 T-0.5 T) at low frequency (<1 kHz) in the third axis direction in the imaging region. Said tertiary magnetic element pair has the required homogeneity (preferably <1 mT) for the magnetic resonance imaging. External "shimming" coils can also be used to achieve this homogeneity. Furthermore, active or passive isolation methods can be applied on at least one pair of magnetic elements in order to prevent "eddy" currents and to reduce the magnetic field interferences originating from outside. Each magnetic element in the tertiary magnetic element pair is fed with co-directional currents and a highly homogenous magnetic field is generated in the third axis direction, so that for magnetic resonance imaging the nuclear spins in the imaging area are aligned parallel or anti-parallel in said direction. Since the number of parallel-aligned spins is slightly higher than the number of anti-parallel aligned spins, net magnetization of spins on the third axis occurs in the positive direction with respect to the coordinate system. The spins rotate around the third axis at the Larmor frequency $f=(\gamma/2\pi)$ B0 determined by the gyromagnetic ratio $(\gamma/2\pi)$ and the magnetic field amplitude (B0). The Larmor frequency for hydrogen protons typically displayed in clinical magnetic resonance imaging is 42.58 MHz/T.

In the magnetic particle imaging method the tertiary magnetic element pair is used to generate the focus field for scanning the magnetic field-free region, preferably the magnetic field-free line, along the first plane. When said tertiary magnetic element pair is not fed, the magnetic field-free region, preferably field-free line, is formed in the coordinate center. The magnetic field that must be applied to shift the magnetic field-free line to the edge of the field of view is calculated by the following formula:

$$B0[T]=R[m]/G\ [T/m]$$

B0 [T]: The magnetic field created by the tertiary magnetic element pair in the field of view,
R [m]: The radius of the field of view,
G [T/m]: The magnetic field gradient of the magnetic field-free region.

For example, B0 should be 0.2 T for a gradient field with a magnetic field change of 1 T/min a 20 cm radius imaging area. For real-time imaging, this magnetic field must be increased and decreased rapidly (1 Hz-1000 Hz). It is possible to generate a magnetic field of this magnitude at high speeds with resistive coils. However, these coils have relatively high resistance and inductance values. High resistance generates excessive heat on coil conductors, and high inductance increases the required driving voltage. The problem of overheating can be solved by liquid cooling method by producing coils with hollow conductive material and circulating liquids, such as water or oil, that will allow heat to be removed from them inside the coils. The inductance value can typically be on the order of tens of mH levels. The voltage needed to drive the coil with variable current is calculated as follows:

$$V[V] = I[A] \cdot R[\Omega] + L[H]\frac{dI}{dt}\left[\frac{A}{s}\right]$$

V [V]: The voltage that must be applied to the electromagnet,
I [A]: The current applied to the electromagnet,
R [Ω]: Electromagnet resistance,
L [H]: Electromagnet inductance, $$\frac{dI}{dt}\left[\frac{A}{s}\right]$$

: Time-dependent derivative of the current applied to the electromagnet.

For example, to drive an electromagnet with a resistance of 200 mΩ and an inductance of 100 mH at a frequency of 1 kHz with 200 Amps, a voltage over 12 kV is required. Since it is difficult to realize this value in practice, at least one filtering and matching circuit can also be used in the inventive arrangement. With this circuit, unwanted high-frequency components on the applied current are eliminated, and also, by harmonizing the operating frequency of the electromagnet, the reactive component is reduced and the applied voltage requirement is reduced. Thus, the coil, i.e. the tertiary magnetic element pair can be fed with the practically applicable voltage and current.

In an embodiment of the invention in which the primary magnetic element pair comprises a first pair of primary magnetic elements forming a magnetic gradient in the direction of the first axis and a second pair of primary magnetic elements forming a magnetic gradient in the direction of the second axis, the first pair of primary magnetic elements forms a magnetic field gradient in the first axis direction. Said first pair of primary magnetic elements generates a magnetic field vector aligned in the third axis direction, but the amplitude of said magnetic field changes linearly in the first axis direction in the imaging field of view. For example, for a first pair of primary magnetic elements forming a 1 T/m gradient in the x-direction; at x=0 the magnetic field is zero, at x=−20 cm the magnetic field is 0.2 T, at x=20 cm the magnetic field is −0.2 T. In an embodiment of the invention, each of the first pair of primary magnetic elements comprises two electromagnets fed with counter-currents in the said first axis direction to generate a gradient in the first axis direction. This electromagnet structure is also called "bi-planar gradient coil".

The second pair of primary magnetic elements, which is also a bi-planar gradient coil structure in the preferred embodiment, generates a magnetic field gradient along the second axis direction. Said second pair of primary magnetic elements again generates a magnetic field vector aligned along the direction of the third axis, but the amplitude of the said magnetic field changes linearly in the second axis direction in the imaging field of view. For example, for the second pair of primary magnetic elements forming a 1 T/m gradient in the y-direction; at y=0 the magnetic field is zero, at y=−20 cm the magnetic field is 0.2 T, at y=20 cm the magnetic field is −0.2 T. In a preferred embodiment of the invention, each of the second primary magnetic element pair comprises two electromagnets fed with countercurrents along the second axis direction to generate a gradient in the second axis direction.

By feeding the first pair of primary magnetic elements and the second pair of primary magnetic elements with different current amplitudes, a gradient can be formed in any desired direction in the imaging plane:

$$I_x(\phi)=(G/\eta_x)\cos\phi,$$

$$I_y(\phi)=(G/\eta_y)\sin\phi$$

$I_x(\phi)$[A]: The current amplitude applied to the first pair of primary magnetic elements for the formation of a magnetic field gradient along the $\phi$ direction,
$I_y(\phi)$[A]: The current amplitude applied to the second pair of primary magnetic elements for the formation of a magnetic field gradient along the $\phi$ direction,
$\eta_x$[T/m/A]: efficiency of the first pair of primary magnetic elements,
$\eta_y$[T/m/A]: efficiency of the second pair of primary magnetic elements,
G [T/m] : The desired magnetic field gradient,
$\phi$: angle between magnetic field gradient direction and the first axis.

In the magnetic resonance imaging process, the first axis and second axis gradients are generated according to the desired sequence with the first pair of primary magnetic elements and the second pair of primary magnetic elements, and in this way the nuclear spin phases and/or frequencies can be manipulated along the direction of the first axis and the second axis. The nuclear spin magnetization signal is collected by the first receiving magnetic element pair by inducing nuclear spins via the transmitting magnetic element pair. Magnetic resonance images can be obtained with a solution in the form of a matrix equation. With this method, imaging and techniques related to high resolution with low high homogeneity magnetic field using permanent magnets for cylindrical openings are explained in detail in the reference document by Cho et al. A New Silent Magnetic Resonance Imaging Using a Rotating DC Gradient, Magnetic Resonance in Medicine, 39: 317-321, 1998. In an alternative embodiment, different trajectories can be scanned with the first pair of primary magnetic elements and the second pair of primary magnetic elements (cartesian, radial, spiral, conical radial, etc.) known in magnetic resonance imaging, and images can be formed by using Fourier transform space reconstruction techniques. In magnetic resonance imaging, the magnetic field distribution with a high homogeneity and the effect of gradients should be known with high precision. For this reason, in alternative embodiments, the arrangement can be provided with corresponding means sensing the amplitude of the said magnetic fields and adjusting the currents of the first pair of primary magnetic elements and the second pair of primary magnetic elements by means of a control loop.

For magnetic particle imaging, the first pair of primary magnetic elements and the second pair of primary magnetic elements generate a selection magnetic field comprising a field-free region, preferably a field-free line, and rotate it to a desired angle as described above. Meanwhile, the tertiary magnetic element pair is excited in order to translate the central axis of the magnetic field-free region on the first plane in any desired direction. Thus, the magnetic field-free region is scanned at different angles and at the central axes in the entire imaging plane, and the magnetic particles in the entire imaging plane can be excited. In addition, the position of the imaging plane in the third axis can be chosen by exciting the first pair of primary magnetic elements and the second pair of primary magnetic elements asymmetrically along the third axis. Thus, three-dimensional imaging can be performed by scanning the magnetic field-free region in a three-dimensional imaging volume.

For magnetic particle imaging, the first pair of primary magnetic elements and the second pair of primary magnetic elements can generate a relatively high gradient in the imaging field of view (>0.1 T /m). Therefore, they need to be fed with higher currents compared to the required currents for magnetic resonance imaging method. Since these electromagnets also have relatively large inductance, a matching and filtering circuit can be used to reduce the reactive voltage at operating frequencies for magnetic particle imaging and to filter unwanted high frequency components. Said electromagnets should generate a relatively low gradient (<50 mT/m) for magnetic resonance imaging. Therefore, they can be driven with much lower current amplitude levels than the current amplitudes required for magnetic particle imaging. For this reason, the first and second pair of primary magnetic element can operate at higher frequency values in magnetic resonance imaging with the same voltage supply used for magnetic particle imaging which provides a means for using different sequences for magnetic resonance imaging.

The secondary magnetic element pair generate a relatively rapidly changing (1 kHz-500 kHz) magnetic field along the third axis. Said secondary magnetic element pair is used as a third axis-gradient electromagnets that enable the selection of the imaging plane on the third axis in magnetic resonance imaging method. To this end, upper and lower parts of the secondary magnetic element pair with respect to the first plane is fed with 180 degrees phase difference. Said secondary magnetic element pair should typically generate a gradient of at most 50 mT/m. A matching and filtering circuit can be used to efficiently drive the secondary magnetic element pair in the desired frequency range.

The upper and lower parts of the secondary magnetic element pair with respect to the first plane are fed in phase to generate a nearly homogeneous magnetic field in the imaging field for magnetic particle imaging. The generated magnetic field amplitude typically ranges from 1 mT to 20 mT. The highest amplitude value used is determined according to peripheral nerve stimulation and thermal heating thresholds for patient safety. The secondary magnetic element pair is used as the drive field generator, which allows the magnetic field-free region to move rapidly in the first plane and to excite the magnetic particles.

In order to generate the magnetic resonance imaging signal, the nuclear spins must be excited at the Larmor frequency in a direction almost perpendicular to the direction of the highly homogeneous magnetic field. For the recommended highly homogeneous magnetic field range (0.05 T-0.5 T), the said Larmor frequency is between 2.13 MHz-21.3 MHz. The transmitting magnetic element pair provides the excitation of nuclear spins by generating an electromagnetic field in the first plane in linear or circular polarization in the frequency depending on the amplitude of the highly homogeneous magnetic field, i.e. the Larmor frequency. For example, for a magnetic field with a high homogeneity of 0.2 T, the transmitting magnetic element pair should radiate in 8.52 MHz center frequency to excite nuclear spins of the hydrogen atoms. Said transmitting magnetic element pair emit at relatively low power. The design of the transmitting magnetic element pair and its matching to the power supply are such that they operate in a certain bandwidth at the center frequency required by the arrangement. Design alternatives of said transmitting magnetic element pair are available in the state of the art and it is possible that they can be realized in different ways by a skilled person in the art.

The magnetic resonance imaging signal is received by the first receiving magnetic element pair during relaxation of the nuclear spins induced by the transmitting magnetic element pair. The first receiving magnetic element pair is sensitive, i.e. can receive the signals in the direction almost perpendicular to the highly homogeneous magnetic field. In an embodiment of the present invention, the signal received by the first receiving magnetic element pair is received and filtered efficiently via the matching and filtering circuit using a receiving circuit, and amplified via a low noise factor amplifier circuit and sampled via an analog-digital converter. The sampled signal can then be digitally processed and converted into magnetic resonance images by any of the image reconstruction methods known in the art. In alternative embodiments of the invention, the first receiving magnetic element pair can also be positioned close to the imaged area of the body in order to increase sensitivity.

For magnetic particle imaging, the magnetization response of the excited magnetic particles is detected by the secondary magnetic element pair or a second receiving magnetic element pair, or using a magnetic field sensor such as an atomic magnetometer. The second receiving magnetic element pair must be isolated from the secondary magnetic element pair, as the second receiving magnetic element pair is receiving signals while the secondary magnetic element pair is excited. Preferably, a gradiometer type of coil structure can be used for insulation. It is also known in the art to sample the received signal by passing it through a filter that filters the drive field frequency. Magnetic particles excited by the secondary magnetic element pair provide a magnetization response containing frequency spectrum components (e.g. harmonics) outside the drive field frequency in addition to the drive field frequency due to their non-linear magnetic properties. In the magnetic particle imaging method, since the drive field is also coupled to the received signal detected by the receiving magnetic element pair(s), drive field frequency component is preferably discarded with a notch or a high-pass filter. The signal is then sampled by passing it through a low noise amplifier. The sampled signal can be transformed into images of MNP distribution in the imaging field of view using two different reconstruction methods known in the art: projection reconstruction method using the mathematical model of the signal (K. Bente, M. Weber, M. Graeser, T F Sattel, M. Erbe and T M Buzug, "Electronic Field Free Line Rotation and Relaxation Deconvolution in Magnetic Particle Imaging," in IEEE Transactions on Medical Imaging, vol. 34, no. 2, pp. 644-651, Feburary 2015), or the system matrix reconstruction method based on calibration measurements (Gleich, B. and Weizenecker, J. (2005), "Tomographic imaging using the nonlinear response of magnetic particles" in Nature, vol. 435, pp.1214-121'7).

BRIEF DESCRIPTION OF THE DRAWINGS

The arrangement that allows performance of both magnetic particle imaging and magnetic resonance imaging and the device comprising said arrangement realized to attain the aim of the present invention are illustrated in the attached figures, where.

Figure 1:
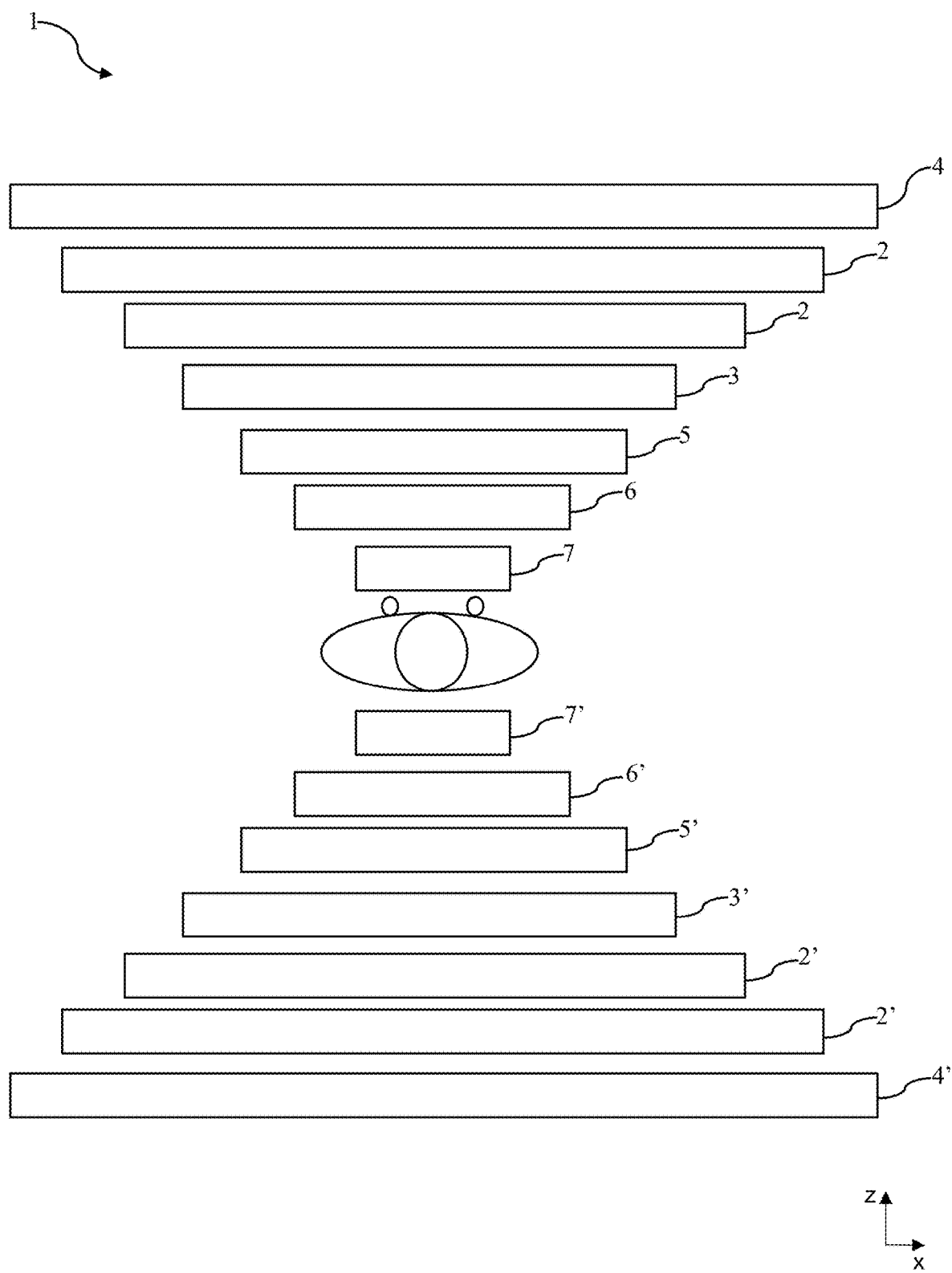
FIG. 1—is the schematic view of an embodiment of the inventive arrangement.
Figure 2:
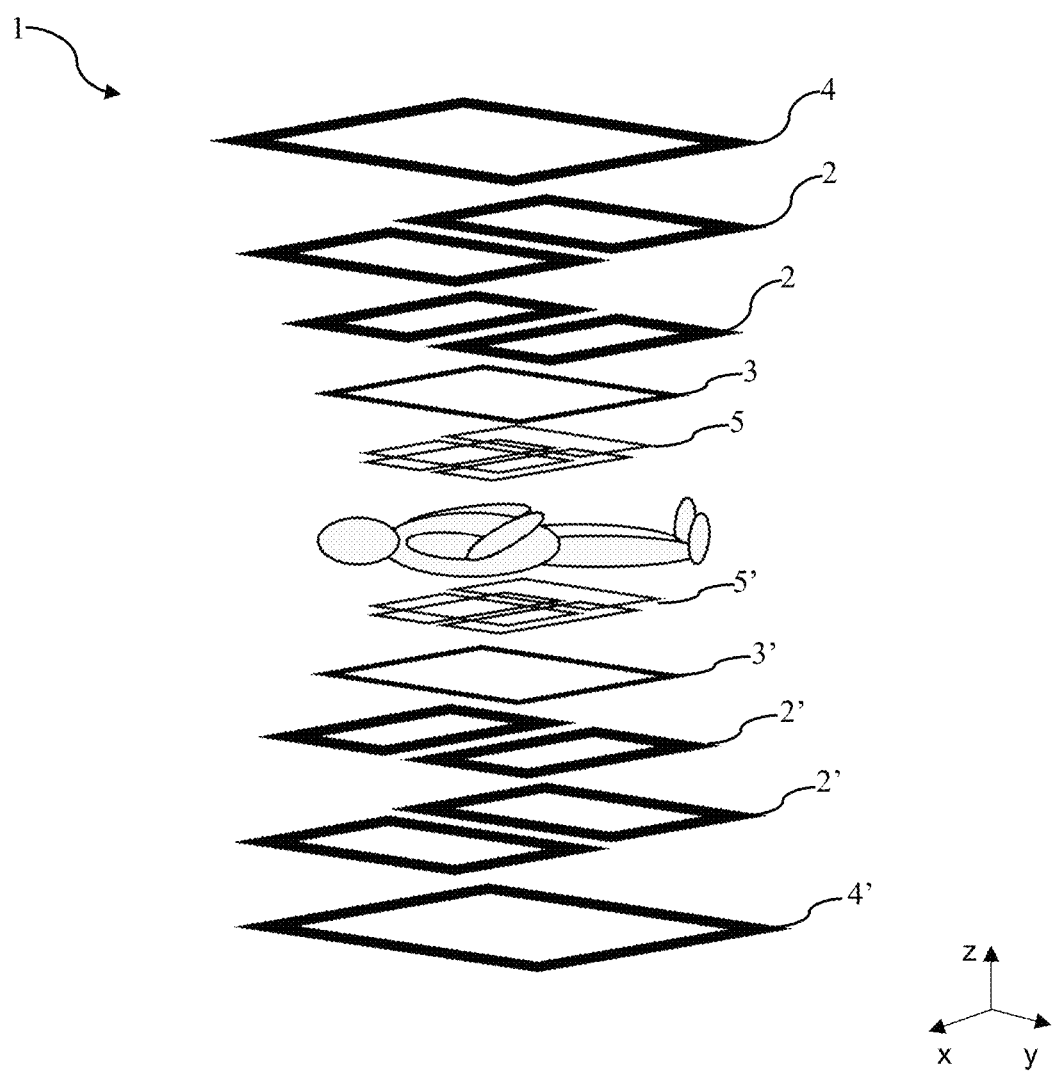
FIG. 2—is the schematic perspective view of the elements forming a magnetic field in an embodiment of the inventive arrangement.
Figure 3:
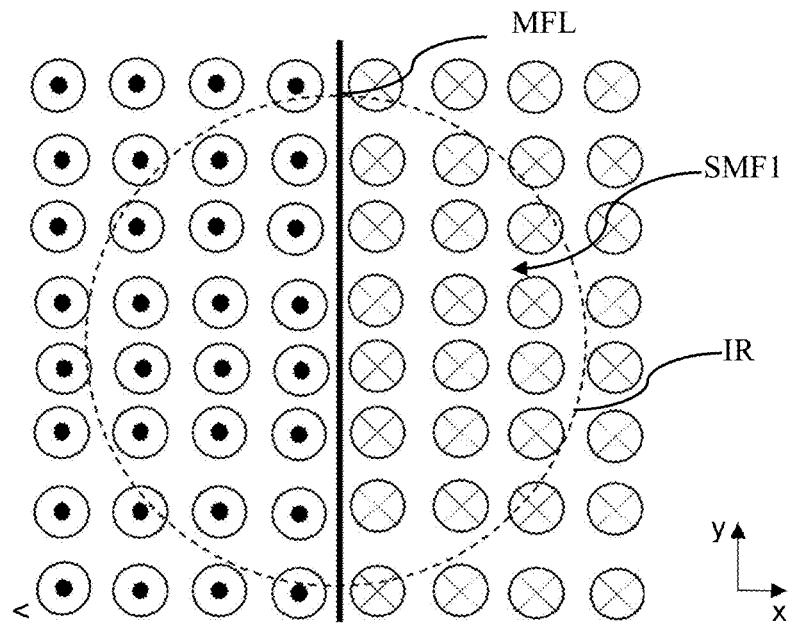
FIG. 3—is a graph showing the magnetic field vector and the corresponding magnetic field-free line formed on the first plane along the first axis direction of the imaging area by the primary magnetic element pair by means of the inventive arrangement.
Figure 4:
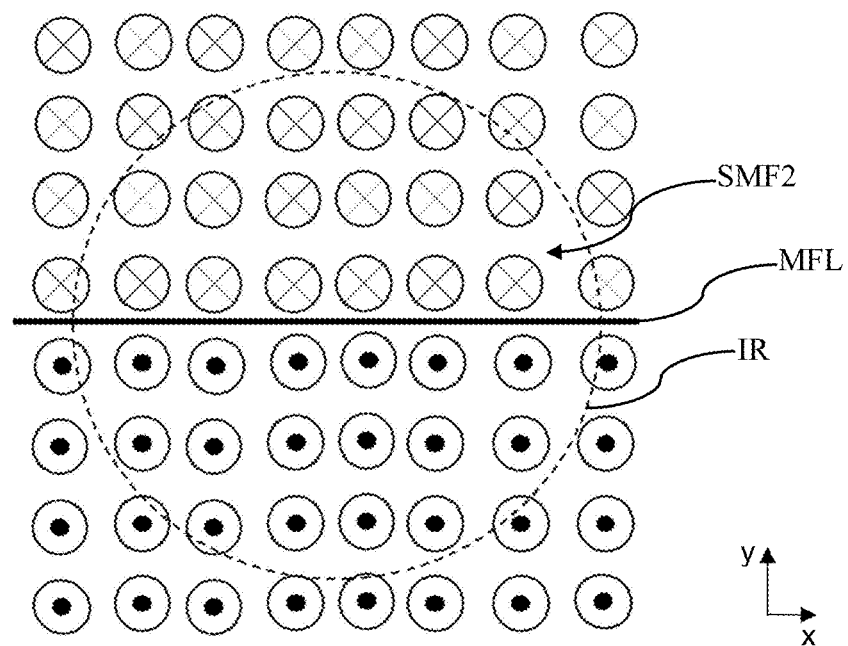
FIG. 4—is a graph showing the magnetic field vector and the corresponding magnetic field-free line formed on the first plane along the second axis direction of the imaging area by the primary magnetic element pair by means of the inventive arrangement.
Figure 5:
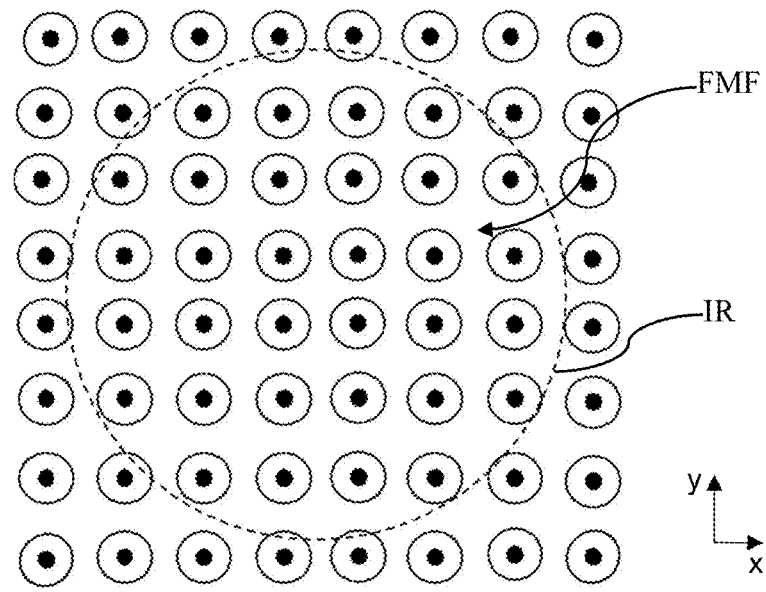
FIG. 5—is a graph showing the homogeneous magnetic field vector formed in the imaging area by the tertiary magnetic element pair on the first plane by means of the inventive arrangement.
Figure 6:
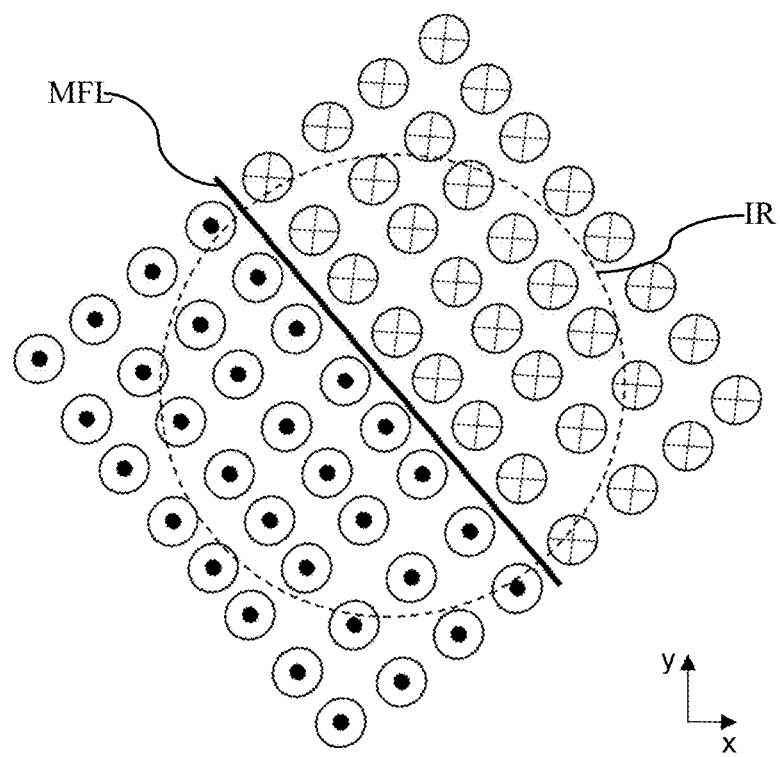
FIG. 6—is a graph showing the magnetic field vector and the corresponding magnetic field-free line formed in a direction that is rotated to an angle around the third axis in the imaging region by the primary magnetic element pair on the first plane by means of the inventive arrangement.
Figure 7:
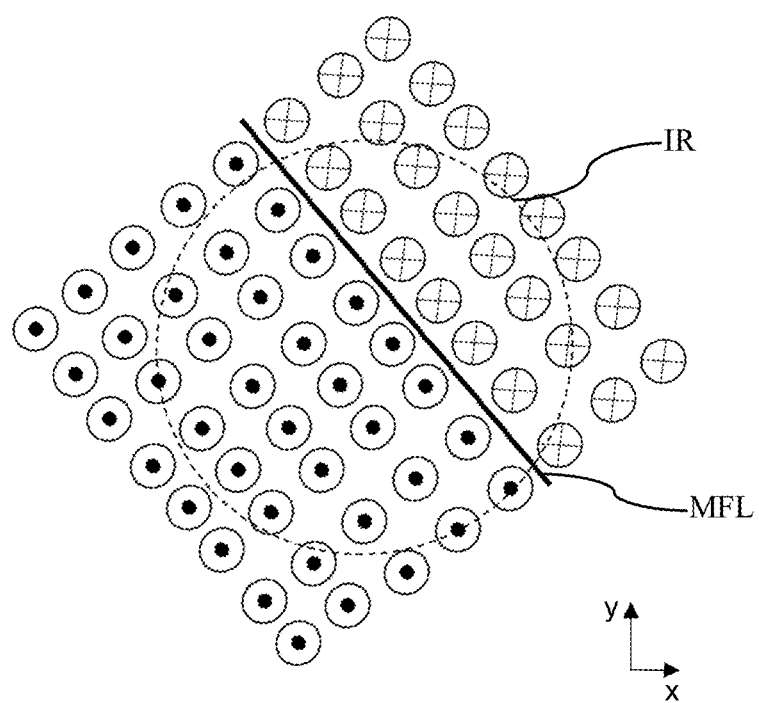
FIG. 7—is a graph showing the magnetic field vector and the corresponding magnetic field-free line rotated to an angle around the third axis in the imaging region by the primary magnetic element pair in the primary plane and shifted on the first plane with the tertiary magnetic element pair by means of the inventive arrangement.
Figure 8:
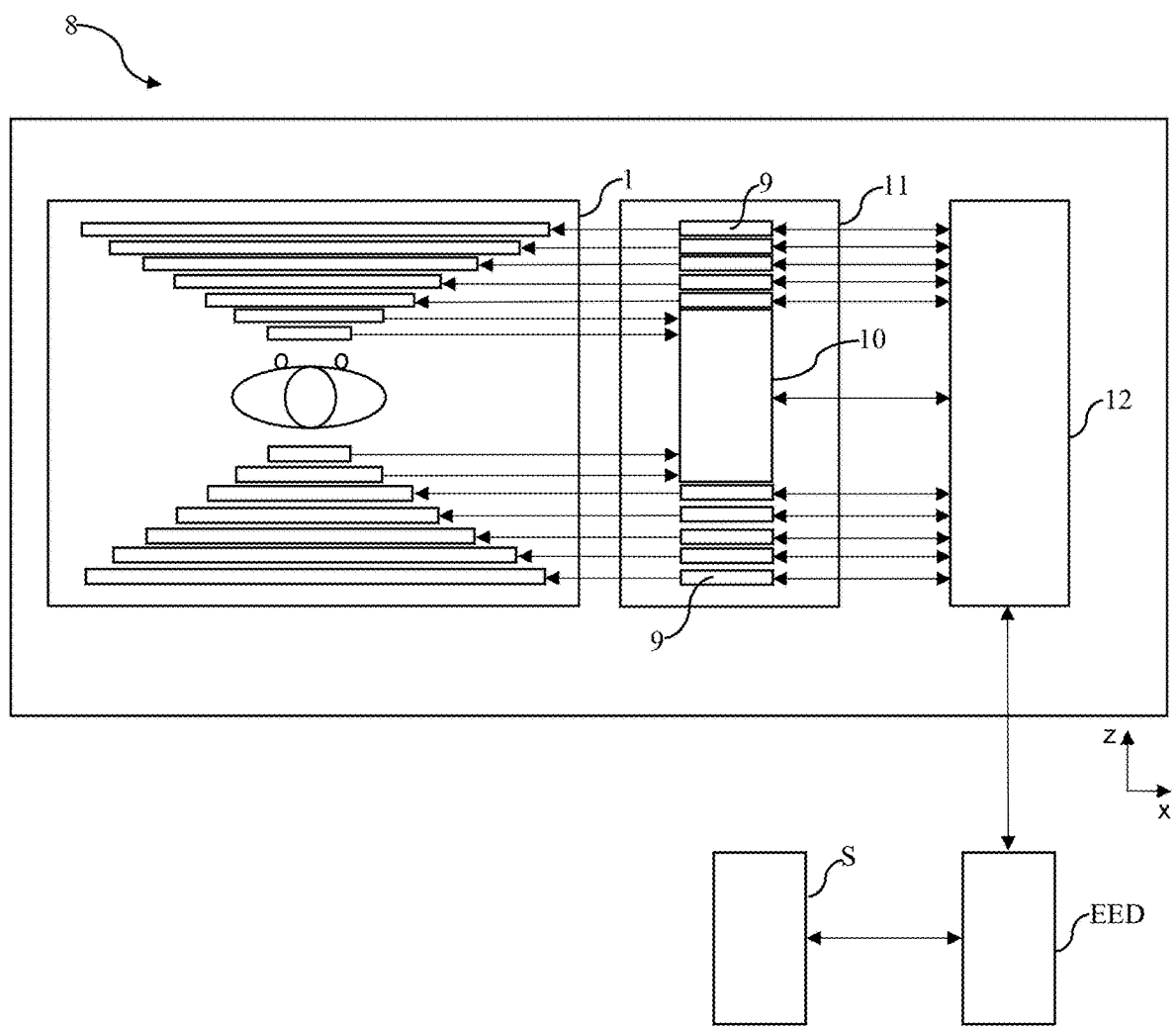
FIG. 8—is the schematic view of an embodiment of a device comprising the inventive arrangement.

The elements illustrated in the figures are numbered individually as follows:

1. Arrangement
2-2'. Primary magnetic element pair
3-3'. Secondary magnetic element pair
4-4'. Tertiary magnetic element pair
5-5'. Transmitting magnetic element pair
6-6'. First receiving magnetic element pair
7-7'. Second receiving magnetic element pair
8. Device
9. Driving circuit 10. Receiving circuit
11. Driver unit
12. Control unit
13. Current source
14. First matching and filtering circuit
15. Second matching and filtering circuit
16. Amplifier circuit
17. Analog/digital converter
X. First axis
Y. Second axis
Z. Third axis
IR. Imaging region
MFL. Magnetic field-free line
SMF1. The selection magnetic field created along the direction of the first axis for magnetic particle imaging or the magnetic field gradient created along the direction of the first axis for magnetic resonance imaging
SMF2. The selection magnetic field generated along the direction of the second axis for magnetic particle imaging or the magnetic field gradient generated along the direction of the second axis for magnetic resonance imaging
FMF. The focus magnetic field created for magnetic particle imaging or homogeneous magnetic field created for magnetic resonance imaging
EED. External electronic device
S. Screen
I. First angle
II. Second angle
N. $n^{th}$ angle
MPG. Magnetic particle imaging phase
MRI. Magnetic resonance imaging phase

DETAILED DESCRIPTION OF THE EMBODIMENTS

An arrangement (1) that enables performance of both magnetic particle imaging and magnetic resonance imaging comprises; at least one primary magnetic element pair (2-2') configured to generate a selection magnetic field (SMF1/SMF2) in the imaging region (IR) on which the imaging is to be performed for magnetic particle imaging, at least one secondary magnetic element pair (3-3') configured to generate a drive magnetic field, and at least one tertiary magnetic elements pair (4-4') configured to generate a focus magnetic field (FMF). The primary magnetic element pair (2-2') generates an inhomogeneous selection magnetic field (SMF1) in which at least one magnetic field is almost zero. The primary magnetic element pair (2-2') is configured to generate the selection magnetic field (SMF1), preferably comprising a magnetic field-free line (MFL), and to rotate it to the desired angle. The secondary magnetic element pair (3-3') generates the drive magnetic field that changes with time to dynamically change the magnetization of the particles in the imaging region (IR) on a first plane formed by a first axis (X) and a second axis (Y) substantially perpendicular to the first axis (X). In an embodiment of the invention, the secondary magnetic element pair (3-3') is also configured to detect the response of the excited magnetic particles. The tertiary magnetic element pair (4-4') generates the focus magnetic field that allows the magnetic field-free region to be displaced along the first plane. In case when the tertiary magnetic element pair (4-4') is not excited, the magnetic field-free region is located in the center of the imaging region (IR). In the magnetic particle imaging process, the magnetization of the magnetic nanoparticles in the magnetic field-free region generated by the primary magnetic element pair (2-2') is dynamically changed by the secondary magnetic element pair (3-3') and the tertiary magnetic element pair (4-4'), and their magnetization response is detected preferably by the secondary magnetic element pair (3-3'), thus enabling magnetic particle imaging to be performed.

In the arrangement (1) of the present invention, the primary magnetic element pair (2-2') is configured to generate a magnetic field gradient (SMF1) on the first plane for magnetic resonance imaging, the secondary magnetic element pair (3-3') is configured to generate a magnetic field gradient on a third axis (Z) perpendicular to the first plane for magnetic resonance imaging, the tertiary magnetic element pair (4-4') is configured to generate a high homogeneity magnetic field (FMF) for magnetic resonance imaging wherein the inventive arrangement (1) also comprises at least one transmitting magnetic element pair (5-5') configured to excite nuclear spins inside the high homogeneity magnetic field (FMF), and at least one first receiving magnetic element pair (6-6') configured to receive magnetic resonance signals from the spins induced for magnetic resonance imaging. When magnetic resonance imaging process is desired to be performed by means of the inventive arrangement (1), a high homogeneity magnetic field (FMF) is generated by applying current to the tertiary magnetic element pair (4-4'); currents are applied to the primary magnetic element pair (2-2') to generate a gradient having a certain angle in the first axis (X) and the second axis (Y) (respectively SMF1 and SMF2). Section selection is made on the third axis (Z) by the secondary magnetic element pair (3-3'). In the meantime, a pulse is applied to the spins by the transmitting magnetic element pair (5-5') and preferably after a while another pulse is applied to the spins by the transmitting magnetic element pair (5-5'). Then, magnetic resonance signal acquisition is performed by means of the primary receiver magnetic element pair (6-6'). The pulses applied by the transmitting magnetic element pair (5-5') are periodically repeated and scanned several times on the same radial line in the k-space. Similar sequence is repeated by generating gradients at different angles by the primary magnetic element pair (2-2'). Magnetic resonance image is obtained by processing the obtained data. This sequence is given as an example for magnetic resonance imaging, and different imaging sequences can be performed by a skilled person in the art.

In a preferred embodiment of the invention, the primary magnetic element pair (2-2') is configured to form a magnetic field gradient having a low frequency, preferably in the range of 0-1000 Hz, and high amplitude, preferably in the range of 0.1 T/m-10 T/m.

In a preferred embodiment of the invention, the secondary magnetic element pair (3-3') preferably has a high frequency in the range of 1 kHz-500 kHz, and configured to generate a low amplitude magnetic field preferably in the range of 1 mT-50 mT and a magnetic field gradient preferably in the range 0.1 mT/m-50 mT/m.

In a preferred embodiment of the invention, the tertiary magnetic element pair (4-4') is configured to form magnetic field gradient having a low frequency, preferably in the range of 0-1000 Hz, and a high amplitude, preferably in the range of 0.05 T-0.5 T.

In a preferred embodiment of the invention, the primary magnetic element pair (2-2') comprises; a first pair of primary magnetic elements configured to form the magnetic field gradient (SMF1) along the first axis (X), and a second pair of primary magnetic elements configured to generate a magnetic field gradient (SMF2) along the second axis (Y) for the magnetic resonance imaging. By this way, the formation of magnetic field gradients along the first axis (X) and the second axis (Y) is performed by independent pairs of magnetic elements, thus the arrangement is provided to have a simpler structure. In another embodiment of the present invention, the primary magnetic element pair (2-2') is rotated around the third axis (Z) preferably by a mechanical component, and the magnetic field gradient is rotated to the desired angle in the imaging region (IR).

In a specific embodiment of the invention, the inventive arrangement (1) comprises; two primary magnetic element pairs (2-2'), single secondary magnetic element pair (3-3'), single tertiary magnetic element pair (4-4'), single transmitting magnetic element pair (5-5'), single first receiving magnetic element pair (6-6'). In this embodiment, the number of components of the inventive arrangement (1), which can perform both magnetic particle imaging and magnetic resonance imaging, is kept at a minimum and a cost advantage is achieved.

In a preferred embodiment of the invention, the inventive arrangement (1) further comprises at least one second receiving magnetic element pair (7-7') configured to receive the excited, i.e. stimulated particle signal for magnetic particle imaging. By this way, the secondary magnetic field pair (3-3') is simply used for generating the time varying driving magnetic field in a first plane on which a first axis (X) and a second axis (Y) substantially perpendicular to the first axis extend, to dynamically change the magnetization of the particles in the imaging region whereas the second receiving magnetic element pair (7-7') is used to receive the relaxation signal of magnetic particles for magnetic particle imaging. Thus, the secondary magnetic field pair (3-3') and therefore the arrangement (1) can be used more effectively.

In a preferred embodiment of the invention, the primary magnetic element pair (2-2') and/or the secondary magnetic element pair (3-3') and/or the tertiary magnetic element pair (4-4') and/or the transmitting magnetic element pair (5-5') and/or the first receiving magnetic element pair (6-6') and/or the second receiving magnetic element pair (7-7') are insulated. By such an insulation, generation of "eddy" currents due to time varying magnetic fields and magnetic field interferences originating from outside can be reduced.

In an embodiment of the present invention, the inventive arrangement (1) further comprises "shimming" coils. By this way, it is ensured that the homogeneity of the magnetic field generated by the tertiary magnetic element pair (4-4') can further be improved, especially for magnetic resonance imaging.

Figure 11:
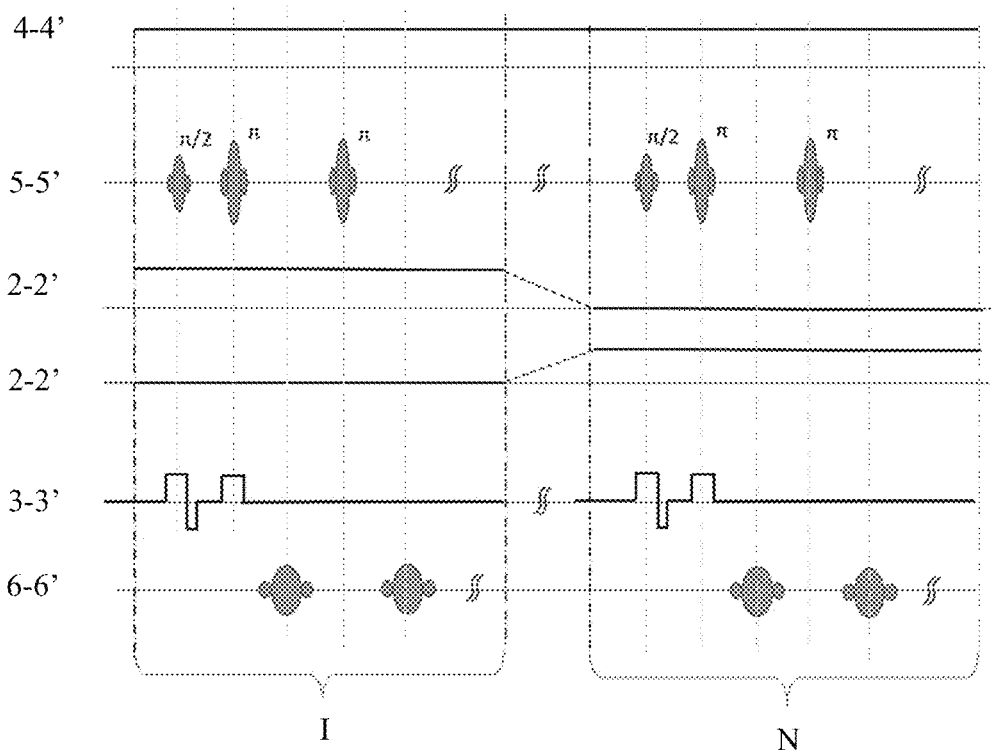
FIG. 11—is a graph showing excitation of magnetic elements for the radial Spin-Echo magnetic resonance imaging sequence.

In an example magnetic resonance imaging radial "spin-echo" sequence, the signal waveform applied to the magnetic elements is illustrated in the graph shown in FIG. 11. In this sequence, a constant current is applied to the tertiary magnetic element pair (4-4') to generate a magnetic field with high homogeneity (FMF); currents are applied to the first primary magnetic element pair and the second primary magnetic element pair (2-2') to generate a gradients (SMF1, SMF2) at a certain angle. Section selection is made on the third axis (Z) by the secondary magnetic element pair (3-3'). In the meantime, a pulse is applied by the transmitting magnetic element pair (5-5'), which tilts the nuclear spins 90 degrees, and after a while, a 180 degree pulse is applied to the nuclear spins by the transmitting magnetic element pair (5-5'). Then, magnetic resonance signal reception is performed by means of the first receiving magnetic element pair (6-6'). The 180-degree pulses are periodically repeated such that the same radial line can be scanned several times in the k-space. Similar sequence is repeated by generating gradients at different angles by the first primary magnetic element pair and the second primary magnetic element pair (2-2'). The obtained data is registered in a rectangular grid by interpolation in the k-space and the image is obtained with 2D inverse FFT (IFFT) transformation. Alternatively, by using the magnetic field (or spatial sensitivity) map generated by magnetic elements and the collected data, the image can be reconstructed iteratively with the projection reconstruction method. For 3-dimensional imaging, different sections can be selected by using a tertiary magnetic element pair (3-3') and scanning can be performed with a similar sequence.

Figure 12:
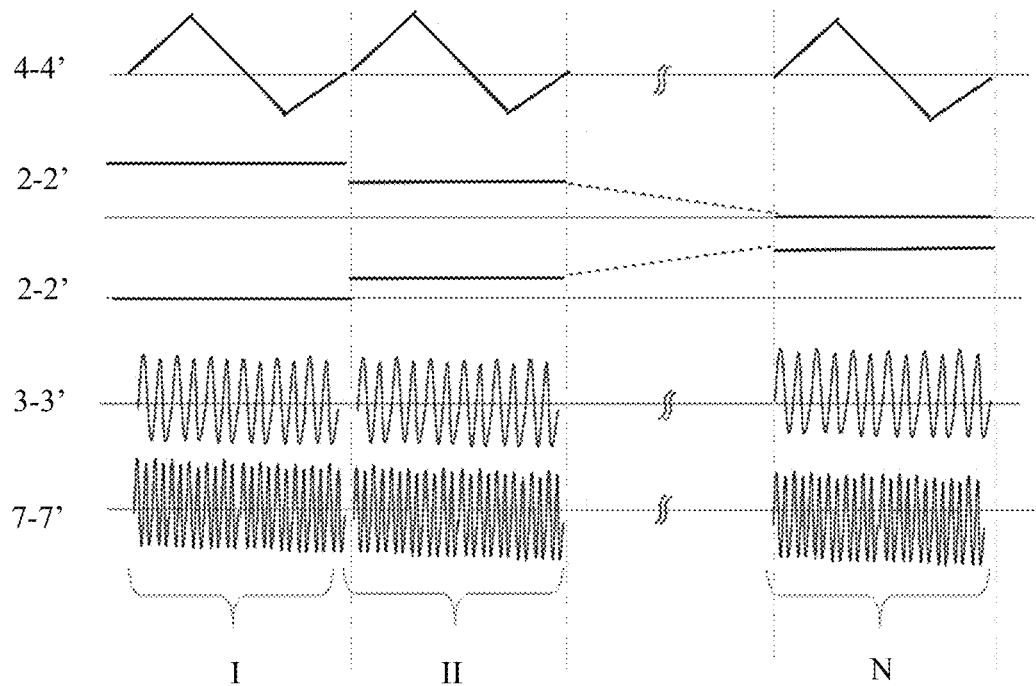
FIG. 12—is a graph showing excitation of magnetic elements for radial magnetic particle imaging trajectory.

For an example radial magnetic particle imaging sequence, the signal waveforms applied to the magnetic elements is illustrated in the graph shown in FIG. 12. In this sequence, currents are applied to the first primary magnetic element pair and the second primary magnetic element pair (2-2') to generate a magnetic field-free line (MFL) at a certain angle. Particles are excited, i.e. stimulated by applying a sine wave to the secondary magnetic element pair (3-3'). It is ensured that the magnetic field-free line (MFL) is scanned in the entire imaging region (IR) by applying triangular waves to the tertiary magnetic element pair (4-4'). In the meantime, preferably the second receiving magnetic element pair (7-7') (or alternatively the secondary magnetic element pair (3-3')) performs the signal acquisition process. Using the received signal, images can be obtained with reconstruction methods known in the art. For three-dimensional imaging, the relevant magnetic elements of the first primary magnetic element pair and the second primary magnetic element pair (2-2') can be excited asymmetrically and the selection area can be similarly scanned in different sections on the third axis (Z).

The aforementioned magnetic resonance imaging and magnetic particle imaging scanning operations can be varied by those skilled in the art. Since there is no switching requirement for switching between magnetic resonance imaging and magnetic particle imaging processes and the imaging regions of these processes are in the same center, sequential magnetic particle imaging and magnetic resonance imaging can be performed without any delay between these operations.

Figure 13:
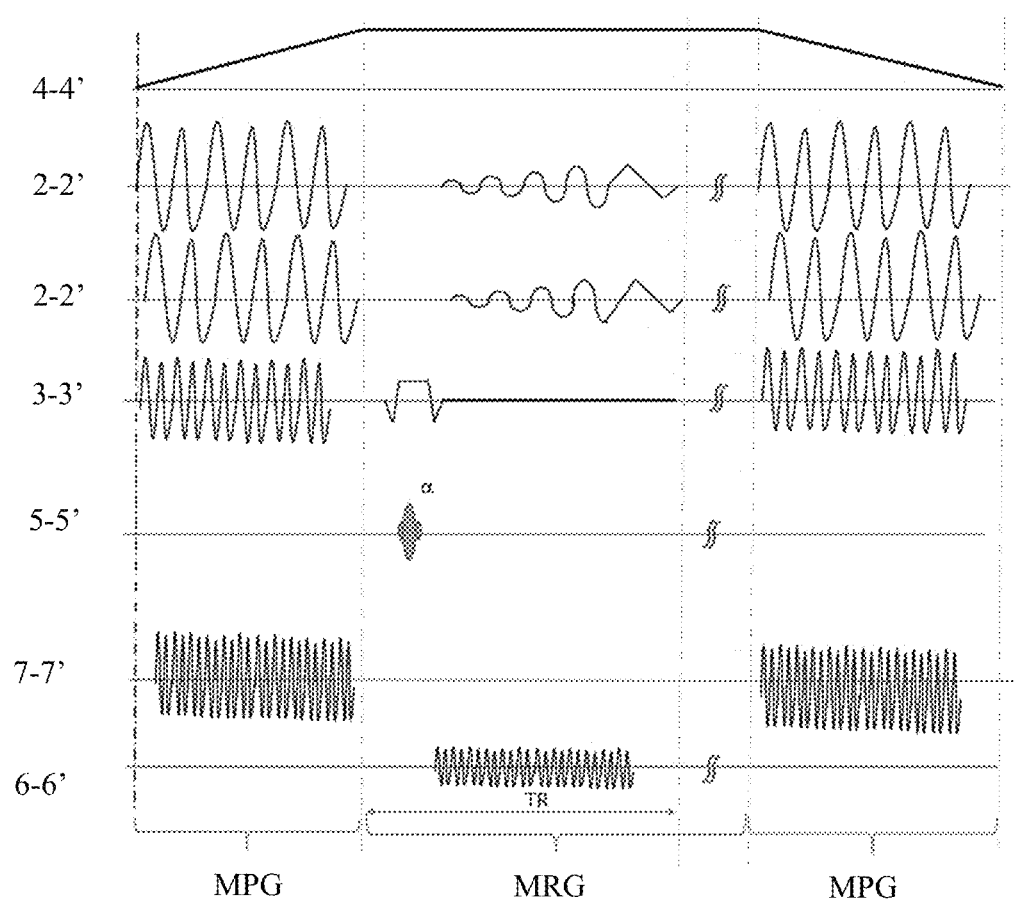
FIG. 13—is a graph showing excitation of magnetic elements for simultaneous Spiral magnetic particle imaging and Spiral B-SSFP magnetic resonance imaging sequence.

The proposed arrangement (1) also allows the use of magnetic particle imaging and magnetic resonance imaging sequences together to obtain anatomical and magnetic particle images simultaneously and present them to the user, and an example sequence for this is illustrated in the graph shown in FIG. 13. In the first magnetic particle-imaging phase (MPG), magnetic particle imaging data is collected. To this end, while a ramp sign is applied to the tertiary magnetic element pair (4-4'), sinusoidal alternating current forms are applied to the first pair of primary magnetic element pair and the second pair of primary magnetic elements pair (2-2'). There is a 90 degree phase difference between the currents applied to the first primary magnetic element pair and the second primary magnetic element pair (2-2'). With these applied currents, the magnetic field-free line (MFL) is moved in a spiral trajectory profile from center of the imaging region (IR) towards the outside. In the meantime, magnetic particles are excited, i.e. stimulated by applying a high frequency driving field via the secondary magnetic element pair (3-3'). Magnetic particle signals are taken from the second receiving magnetic element pair (7-7') simultaneously. In the next phase, i.e. magnetic resonance imaging phase (MRG), the tertiary magnetic element pair (4-4') is kept at the same current and the nuclear spins in the body are magnetized. Spiral Balanced Steady State Free Precession (B-SSFP) sequence for magnetic resonance imaging (Nayak, K S, Hargreaves, B A, Hu, B S, Nishimura, D G, Pauly, J M and Meyer, C H (2005), Spiral balanced steady-state free precession cardiac imaging Magn. Reson. Med., 53: 1468-1473.), data is collected quickly from the entire imaging area. In this sequence, tertiary magnetic element pair (4-4') is used for section selection. Meanwhile, the transmitting magnetic element pair (5-5') applies the pulse that will tilt the magnetization vector of nuclear spins to "alpha ($\alpha$)" degrees. Immediately afterwards, the first primary magnetic element pair and the second primary magnetic element pair (2-2') are excited in such a way to scan a spiral trajectory in the k-space, while the received signal is collected by the first receiving magnetic element pair (6-6'). This sequence can be repeated multiple times in different phases to increase signal strength and improve image resolution. After the magnetic resonance imaging phase (MRI), the imaging mode is switched back to the magnetic particle imaging phase (MPG), this time, the data is collected so that the magnetic field-free line (MFL) trajectory spirals inward. If necessary, these phases are repeated and real-time magnetic particle imaging and magnetic resonance imaging images are obtained and presented to the user simultaneously. In this embodiment, Spiral B-SSFP sequence is used, which allows very fast imaging. The preferred use of the mentioned sequence for cardiovascular and interventional applications is shown in FIG. 13. The use of low amplitude high homogeneity magnetic field in magnetic resonance imaging, has several advantages compared to the use of high amplitude magnetic field (>1 T), especially for fast imaging. In low magnetic field, T1 relaxation is shorter and T2* relaxation is longer, which is suitable for rapid imaging sequences (spiral, conical, EPI (echo planar imaging)) that scan the entire k-space. Since the magnetic resonance frequency is relatively low in low field, problems with body heating or catheter heating are reduced, air-tissue boundaries (sinuses, lungs, intestines, etc.) can be better visualized. Spiral trajectory enables scanning of the k-space with a single pulse. The B-SSFP sequence shortens the scanning time by providing a high signal-to-noise ratio. In addition, it is preferred in cardiac imaging because it enables the separation of heart and blood tissue. In an alternative embodiments of the invention, spiral spin-echo, radial fast low angle-shot (FLASH), echo planar imaging (EPI), under-sampled radial sequences, compressed sensor techniques, and parallel imaging techniques can be used for fast imaging.

The present invention also relates to the use of the above disclosed arrangement (1) in devices suitable for magnetic particle imaging and/or magnetic resonance imaging.

The present invention further relates to a device (8) comprising; the above-described arrangement (1), a plurality of driving circuits (9) configured to apply appropriate current and voltage waveforms to each magnetic element of the primary magnetic element pair (2-2'), the secondary magnetic element pair (3-3'), the tertiary magnetic element pair (4-4') and the transmitting magnetic element pair (5-5') according to the respective magnetic particle imaging or magnetic resonance imaging process and at least one driver unit (11) comprising at least one receiving circuit (10) configured to digitally process the signal received from each magnetic element of the first receiving magnetic element pair (6-6') and the second receiving magnetic element pair (7-7') and at least one control unit (12) configured to control processes in almost real time to generate the current and/or voltage waveform that should be applied to the relevant magnetic elements and to adjust the timings and to monitor the applied current, voltage and temperature values in accordance with the corresponding magnetic particle imaging or magnetic resonance imaging processes and its parameters. The inventive device (8) further comprises a bed or a stretcher like apparatus associated with the arrangement (1) that is configured to perform magnetic particle imaging and magnetic resonance imaging processes and on which the patient to be imaged is positioned wherein each magnetic element of the magnetic element pairs (2-2', 3-3', 4-4', 5-5', 6-6', 7-7') is arranged symmetrically with respect to said apparatus. In a preferred embodiment of the invention, the apparatus has the form of a stretcher that can be accessed from its sides, and the arrangement (1) and apparatus assembly thus resemble for example the open magnetic resonance device existing in the state of the art. In a preferred embodiment of the invention, the control unit (12) is arranged to establish a connection with an external electronic device (EED) such as a computer, and the input can be given to the control unit (12) through the said external electronic device (EED) and data, i.e. magnetic particle images and/or magnetic resonance images can be received from the control unit (12) through said connection. Data received from the control unit (12) can be presented to the relevant parties through a screen (S).

In an embodiment of the present invention, the device (8) further comprises at least one rotation arrangement (not shown in the figures) configured to rotate the primary magnetic element pair (2-2') around the third axis (Z). By rotating the primary magnetic element pair (2-2') around the third axis (Z) by means of said rotating device, the magnetic field gradient formed by said primary magnetic element pair (2-2') can be rotated to the desired angle in the imaging region (IR).

Figure 9:
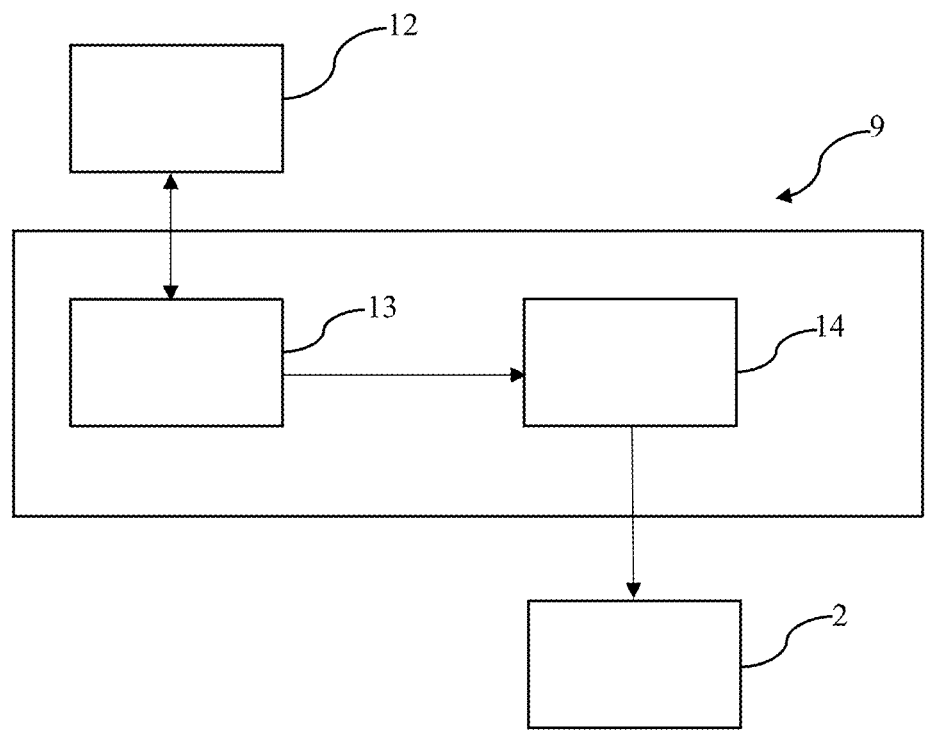
FIG. 9—is the schematic view of an embodiment of a driving circuit in the inventive device.

In an embodiment of the present invention, the driving circuit (9) comprises; at least one current source (13) configured to be operated in a controlled manner according to the process parameters determined by the control unit (12); and at least one first matching and filtering circuit (14) configured to efficiently drive the relevant magnetic element in the specified frequency range determined by the control unit (12) (FIG. 9).

Figure 10:
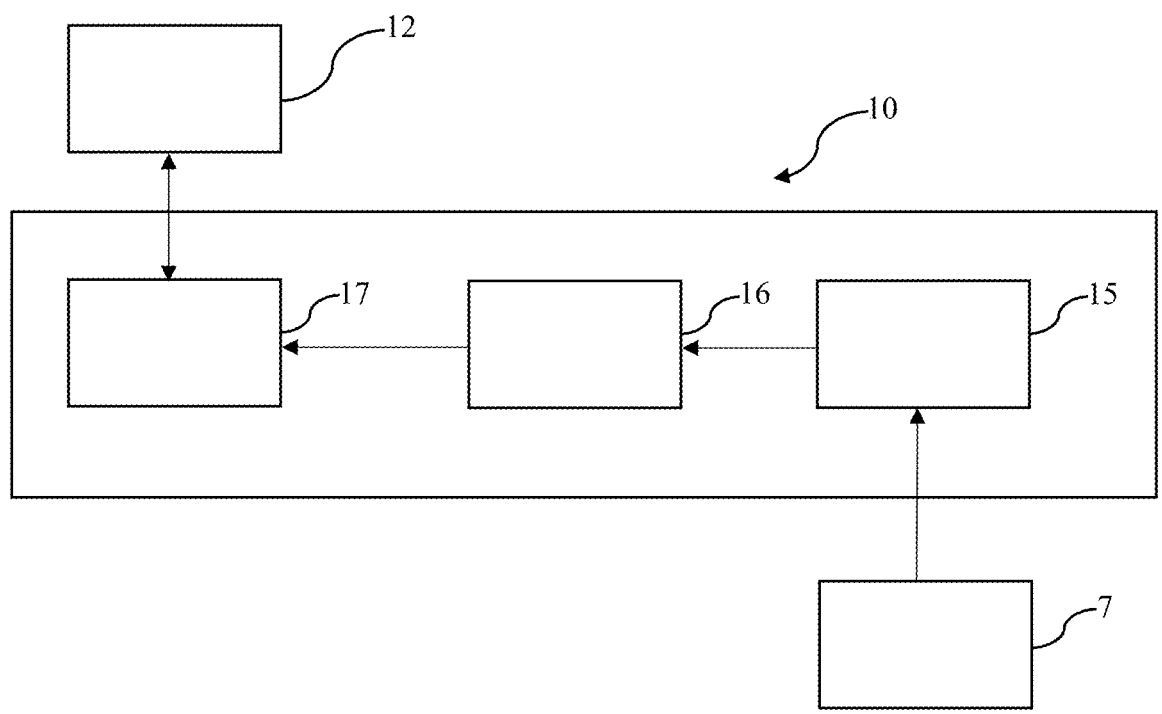
FIG. 10—is the schematic view of an embodiment of a receiving circuit in the inventive device.

In an embodiment of the present invention, the receiving circuit (10) comprises; at least one second matching and filtering circuit (15) configured to receive and filter the magnetic signal of each magnetic element of the first receiving magnetic element pair (6-6') and/or of the second receiving magnetic element pair (7-7'), at least one amplifier circuit (16) configured to amplify the signal filtered by the second matching and filtering circuit (15) and at least one analog/digital converter (17) configured to sample and send the amplified signal to the control unit (12) (FIG. 10).

By means of the inventive arrangement (1), it is ensured that both magnetic particle imaging and magnetic resonance imaging processes can be carried out by the single arrangement (1) by using common equipment for both processes whenever possible. With the inventive arrangement (1), it is possible to switch quickly between magnetic particle imaging and magnetic resonance imaging processes, while magnetic particle imaging and magnetic resonance imaging scanning can be performed rapidly so as to create images and simultaneously display the created images to the users.

Within these basic concepts; it is possible to develop a wide variety of embodiments of the inventive arrangement (1) which enables performance of both magnetic particle imaging and magnetic resonance imaging, and the device (8) comprising said arrangement (8); the invention cannot be limited to the examples disclosed herein, it is essentially according to claims.

The invention claimed is:

1. An arrangement for performing both magnetic particle imaging and magnetic resonance imaging, comprising:
   at least one primary magnetic element pair configured to generate a selection magnetic field (SMF1/SMF2),
   at least one secondary magnetic element pair configured to generate a driving magnetic field,
   at least one tertiary magnetic element pair configured to form a focus magnetic field (FMF) in an imaging region (IR) for the magnetic particle imaging,
   wherein the at least one primary magnetic element pair is configured to generate a first magnetic field gradient (SMF1/SMF2) in a first plane, and a first axis (X) and a second axis (Y) substantially perpendicular to the first axis (X) extend on the first plane,
   in the same imaging region (IR) for the magnetic particle imaging, the at least one secondary magnetic element pair is configured to generate a second magnetic field gradient in
   a third axis (Z) substantially perpendicular to the first plane for the magnetic resonance imaging,
   the at least one tertiary magnetic element pair is configured to form a first high homogeneity magnetic field (FMF) for the magnetic resonance imaging,
   at least one transmitting magnetic element pair configured to excite nuclear spins in a second high homogeneity magnetic field (FMF) for the magnetic resonance imaging, and
   at least one first receiving magnetic element pair configured to receive magnetic resonance signals from the excited nuclear spins for the magnetic resonance imaging.

2. The arrangement according to claim 1, wherein the at least one primary magnetic element pair is configured to form the first magnetic field gradient of low frequency in a range of 0-1000 Hz and of high amplitude in a range of 0.1 T/m-10 T/m.

3. The arrangement according to claim 1, wherein the at least one secondary magnetic element pair is configured to generate a high-frequency low-amplitude magnetic field ranging from 1 mT to 50 mT in a range of 1 kHz to 500 kHz and the second magnetic field gradient in a range 0.1 mT/m to 50 mT/m.

4. The arrangement according to claim 1, wherein the at least one tertiary magnetic element pair is configured to form a third magnetic field gradient of low frequency in a range of 0-1000 Hz and of high amplitude in a range 0.05 T-0.5 T.

5. The arrangement according to claim 1, wherein the at least one primary magnetic element pair comprises:
   a first primary magnetic element pair configured to form a fourth magnetic field gradient (SMF1) along the first axis (X), and
   a second primary magnetic element pair configured to generate a fifth magnetic field gradient (SMF2) along the second axis (Y) for the magnetic resonance imaging.

6. The arrangement according to claim 5, comprising:
   two primary magnetic element pairs namely the first primary magnetic element pair and the second primary magnetic element pair;
   a single secondary magnetic element pair;
   a single tertiary magnetic element pair;
   a single transmitting magnetic element pair; and
   a single first receiving magnetic element pair.

7. The arrangement according to claim 1, wherein at least one second receiving magnetic element pair is configured to receive an excited particle signal for the magnetic particle imaging.

8. The arrangement according to claim 7, wherein an isolation is applied on the at least one primary magnetic element pair and/or the at least one secondary magnetic element pair and/or the at least one tertiary magnetic element pair and/or the at least one transmitting magnetic element pair and/or the at least one first receiving magnetic element pair and/or the at least one second receiving magnetic element pair in order to prevent eddy currents and to reduce magnetic field interferences originating from outside.

9. The arrangement according to claim 1, wherein shimming coils provide extra enhancement of the first high homogeneity magnetic field created by the at least one tertiary magnetic element pair especially in the magnetic resonance imaging.

10. A method for using the arrangement according to claim 1, comprising: applying the arrangement to a device suitable for the magnetic particle imaging and/or the magnetic resonance imaging.

11. A device, comprising
    the arrangement according to claim 1,
    a plurality of driving circuits to apply the current and voltage waveform to relevant magnetic elements of the at least one primary magnetic element pair, the at least one secondary magnetic element pair, the at least one tertiary magnetic element pair, the at least one transmitting magnetic element pair according to the corresponding magnetic particle imaging or the magnetic resonance imaging;
    at least one drive unit comprising at least one receiving circuit configured to process and convert a signal received from each magnetic element of the at least one first receiving magnetic element pair and the at least one second receiving magnetic element pair into a digital signal; and
    at least one control unit configured to generate the current and/or voltage waveform that can be applied to the relevant magnetic elements, to adjust the timings and to monitor the applied current, voltage and temperature values in order to control the processes in almost real time in accordance with the magnetic particle imaging or the magnetic resonance imaging and parameters of the magnetic particle imaging or the magnetic resonance imaging.

12. The device according to claim 11, wherein at least one rotation arrangement is configured to rotate the at least one primary magnetic element pair around the third axis (Z).

13. The device according to claim 11, wherein each of the plurality of driving circuits comprising:
    at least one current source configured to be operated in a controlled manner according to process parameters determined by the at least one control unit, and
    at least one first matching and filtering circuit configured to efficiently drive the relevant magnetic element in a certain frequency range determined by the control unit.

14. The device according to claim 11, wherein the at least one receiving circuit comprising
    at least one second matching and filtering circuit configured to receive and filter a signal induced on each magnetic element of the at least one first receiving magnetic element pair and/or of the at least one second receiving magnetic element pair in a magnetic particle imaging process and/or a magnetic resonance imaging process; and at least one amplifier circuit configured to amplify a signal filtered by the at least one second matching and filtering circuit, and at least one analog/digital converter configured to sample and send the amplified signal to the at least one control unit.

15. The arrangement according to claim 2, wherein the at least one secondary magnetic element pair is configured to generate a high-frequency low-amplitude magnetic field ranging from 1 mT to 50 mT in a range of 1 kHz to 500 kHz and the second magnetic field gradient in a range 0.1 mT/m to 50 mT/m.

16. The arrangement according to claim 2, wherein the at least one tertiary magnetic element pair is configured to form a third magnetic field gradient of low frequency in a range of 0-1000 Hz and of high amplitude in a range 0.05 T-0.5 T.

17. The arrangement according to claim 3, wherein the at least one tertiary magnetic element pair is configured to form a third magnetic field gradient of low frequency in a range of 0-1000 Hz and of high amplitude in a range 0.05 T-0.5 T.

18. The arrangement according to claim 2, wherein the at least one primary magnetic element pair comprises:

a first primary magnetic element pair configured to form a fourth magnetic field gradient (SMF1) along the first axis (X), and a second primary magnetic element pair configured to generate a fifth magnetic field gradient (SMF2) along the second axis (Y) for the magnetic resonance imaging.

19. The arrangement according to claim 3, wherein the at least one primary magnetic element pair comprises:

a first primary magnetic element pair configured to form a fourth magnetic field gradient (SMF1) along the first axis (X), and a second primary magnetic element pair configured to generate a fifth magnetic field gradient (SMF2) along the second axis (Y) for the magnetic resonance imaging.

20. The arrangement according to claim 4, wherein the at least one primary magnetic element pair comprises:

a first primary magnetic element pair configured to form a fourth magnetic field gradient (SMF1) along the first axis (X), and a second primary magnetic element pair configured to generate a fifth magnetic field gradient (SMF2) along the second axis (Y) for the magnetic resonance imaging.

\* \* \* \* \*